(12) United States Patent
Lewandowski et al.

(10) Patent No.: US 7,384,984 B2
(45) Date of Patent: *Jun. 10, 2008

(54) REACTIVE HYDROPHILIC OLIGOMERS

(75) Inventors: Kevin M. Lewandowski, Inver Grove Heights, MN (US); Duane D. Fansler, Dresser, WI (US); Michael S. Wendland, North St. Paul, MN (US); Steven M. Heilmann, Afton, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 791 days.

This patent is subject to a terminal disclaimer.

(21) Appl. No.: 10/732,715

(22) Filed: Dec. 10, 2003

(65) Prior Publication Data

US 2005/0131148 A1   Jun. 16, 2005

(51) Int. Cl.
*A61K 47/00* (2006.01)
(52) U.S. Cl. .............................. 514/772.1; 514/772.3; 514/72.6; 424/400
(58) Field of Classification Search .................. None
See application file for complete search history.

(56) References Cited

U.S. PATENT DOCUMENTS

| | | |
|---|---|---|
| RE24,906 E | 12/1960 | Ulrich |
| 3,121,021 A | 2/1964 | Copeland |
| 3,389,827 A | 6/1968 | Abere et al. |
| 4,094,842 A | 6/1978 | Wenzel et al. |
| 4,112,213 A | 9/1978 | Waldman |
| 4,123,423 A | 10/1978 | Wenzel et al. |
| 4,190,566 A | 2/1980 | Noll et al. |
| 4,385,164 A | 5/1983 | Sinclair et al. |
| 4,499,896 A | 2/1985 | Heinecke |
| 4,598,004 A | 7/1986 | Heinecke |
| 4,680,352 A | 7/1987 | Janowicz et al. |
| 4,694,054 A | 9/1987 | Janowicz |
| 4,849,458 A | 7/1989 | Reed et al. |
| 5,362,826 A | 11/1994 | Berge et al. |
| 5,506,279 A | 4/1996 | Babu et al. |
| 5,531,855 A | 7/1996 | Heinecke et al. |
| 5,614,310 A | 3/1997 | Delgado et al. |
| 5,653,699 A | 8/1997 | Reed et al. |
| 5,733,570 A | 3/1998 | Chen et al. |
| 5,738,642 A | 4/1998 | Heinecke et al. |
| 5,741,543 A | 4/1998 | Winslow et al. |
| 5,773,534 A | 6/1998 | Antonelli et al. |
| 5,849,325 A | 12/1998 | Heinecke et al. |
| 5,902,836 A | 5/1999 | Bennett et al. |
| 6,007,833 A | 12/1999 | Chudzik et al. |
| 6,171,985 B1 | 1/2001 | Joseph et al. |
| 6,198,016 B1 | 3/2001 | Lucast et al. |
| 6,221,303 B1 | 4/2001 | Steinmann |
| 6,361,768 B1 | 3/2002 | Galleguillos et al. |
| 6,448,301 B1 | 9/2002 | Gaddam et al. |
| 6,559,223 B2 | 5/2003 | Green et al. |
| 6,635,690 B2 | 10/2003 | Heilmann et al. |
| 6,664,306 B2 | 12/2003 | Gaddam et al. |
| 2001/0051178 A1 | 12/2001 | Blatchford et al. |
| 2003/0203011 A1 | 10/2003 | Abuelyaman et al. |
| 2003/0212210 A1 | 11/2003 | Heilmann et al. |
| 2003/0216519 A1 | 11/2003 | Heilmann et al. |
| 2004/0063027 A1 | 4/2004 | Barr et al. |
| 2005/0070688 A1 | 3/2005 | Lewandowski et al. |
| 2006/0165762 A1 | 7/2006 | Plaut et al. |
| 2006/0292209 A1 | 12/2006 | Lewandowski et al. |

FOREIGN PATENT DOCUMENTS

| | | |
|---|---|---|
| WO | WO 99/13865 | 3/1999 |
| WO | WO 99/13866 | 3/1999 |
| WO | WO 00/42958 | 7/2000 |
| WO | WO 01/18079 A1 | 3/2001 |
| WO | WO 01/60296 A1 | 8/2001 |
| WO | WO 03/086493 A1 | 10/2003 |
| WO | WO 2005/035607 A1 | 4/2005 |

OTHER PUBLICATIONS

Scott et al., Highly crosslinked, PEG-containing copolymers for sustained solute delivery Biomaterials 20(1999) 1371-1380.*
Nguyen et al., Photopolymerizable hydrogels for tissue engineering applications Biomaterials 23(2002) 4307-4314.*
Oduin, Principles of Polymerization 1991 A19-23.*
G. Odian, *Principles of Polymerization*, 3rd edition, 1991, John Wiley & Sons, New York, pp. 108.
G. P. Gladyshev and K. M. GIbov, *Polymerization at Advanced Degrees of Conversion*, Keter Press, Jerusaled, (1970).
Protective Groups in Organic Synthesis, T. Greene and P.G.M. Wuts, Eds., 3rd edition, Wiley Interscience, New York, N.Y., 1999.
U.S. Appl. No. 10/792,238, filed Mar. 2, 2004, entitled "Crosslinkable Hydrophilic Materials From Reactive Oligomers Having Pendent Unsaturated Groups".
U.S. Appl. No. 10/790,902, filed Mar. 1, 2004, entitled "Crosslinkable Hydrophilic Materials From Reactive Oligomers Havign Pendent Photoinitiator Groups".
Odian, "Principles of Polymerization", (1991), pp. 19-24, 3rd Edition, John Wiley & Sons, Inc., New York.

* cited by examiner

*Primary Examiner*—Michael G. Hartley
*Assistant Examiner*—Eric E. Silverman
(74) *Attorney, Agent, or Firm*—Kent S. Kokkko

(57) ABSTRACT

Hydrophilic compositions are described, which are prepared from a first component oligomer containing pendent hydrophilic groups and pendent reactive functional groups capable of reaction at effective rates (at normal processing temperatures), with a co-reactive second component possessing functionality that is complementary to that of the first oligomer. The compositions may be used as in preparation of hydrophilic gel coatings or layers for medical devices.

42 Claims, No Drawings

REACTIVE HYDROPHILIC OLIGOMERS

TECHNICAL FIELD OF THE INVENTION

This invention relates to novel step growth, hydrophilic, crosslinkable oligomer compositions and articles prepared therefrom. The compositions are useful in preparing gel materials and medical articles incorporating such materials, particularly medical articles useful as wound dressings.

BACKGROUND OF THE INVENTION

Historically, exudate from a wound has been treated by absorbing it using a dressing containing an absorbent material. Typical dressings contain a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

More recently the use of so-called "occlusive" dressings for pressure sores and ulcers has gained acceptance. Most of these products are formed from several layers, including at least an inner skin-contacting layer and an outer backing layer. The dressing is applied as a cover for the sore or ulcer in a size providing a margin around the wound area that adhesively seals to the skin. An inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

A wound care product in current use utilizes a hydrocolloid absorbent. Such a material typically has poor transparency so that the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

SUMMARY OF THE INVENTION

Though there are known hydrophilic gel materials useful in medical applications such as wound dressings, many do not have the appropriate balance of absorption and cohesive strength. Thus, additional such materials are needed. Further, it can be desirable to provide an occlusive material that is also transparent and/or flexible for use in a medical article such as a wound dressing or wound packing material. Yet further, it can be desirable to provide compositions that are melt-processable.

The current invention describes reactive, melt-processable materials that can be cured by a variety of step-growth mechanisms to yield uniform coatings, particularly gel coatings. The component oligomers and extent of reaction, or crosslink density, can be varied in order to provide specific properties for a range of applications. The molecular weight of these materials is such that they can easily be processed, giving economic and environmental advantages. The materials can subsequently be cured through application of heat to yield improved final mechanical properties, without the thickness and exposure limitations imposed by radiation curing. Thus, these materials represent a significant advance of the current art.

Briefly, the present invention provides novel hydrophilic, oligomeric compositions prepared from a first oligomer containing pendent hydrophilic groups and pendent functional groups, and a co-reactive second component oligomer having pendent co-reactive functional groups. The second component oligomer may further comprise polymerizable monomer units having pendent hydrophilic groups. Alternatively, the composition may further comprise a third component step-growth catalyst. The compositions can be melt-processable.

In one aspect this invention provides a step growth curable oligomer composition comprising a) a first component oligomer, having a carbon-carbon backbone, comprising a plurality of polymerized monomer units comprising pendant reactive nucleophilic or electrophilic functional groups, and pendent, hydrophilic poly(alkylene oxide) groups;

b) a second polyfunctional component co-reactive with said first component oligomer comprising a second oligomer, having a carbon-carbon backbone, comprising a plurality of polymerized monomer units comprising pendent functional groups co-reactive with said pendant reactive nucleophilic or electrophilic functional groups of said first component oligomer, and optionally pendent, hydrophilic poly(alkylene oxide) groups;

and preferably at least one of a) and b) has a functionality of greater than 2, and preferably the composition is melt-processable at temperatures of 100° C. or less.

The present invention provides novel compositions prepared from a first oligomer containing reactive functional groups capable of reaction at effective rates (at normal processing temperatures) with a co-reactive second component possessing functionality that is complementary to that of the first oligomer. By complementary it is meant that if the oligomer's reactive functional groups are electrophilic in nature, the second component should possess co-reactive nucleophilic groups. The converse is also useful; when the oligomer contains reactive nucleophilic groups then the second component contains co-reactive electrophilic groups. In addition, reactions involving oligomeric reactants of the instant invention are controlled and precise in that they result in oligomer-oligomer coupling reactions only by reaction between the reactive and co-reactive functional groups.

In another aspect, this invention provides a process of preparing a novel composition which comprises the steps of providing the novel oligomer composition of this invention, preferably further comprising an effective amount of a step-growth catalyst, and subjecting said composition to sufficient thermal energy to crosslink the first component oligomer and second component oligomer by forming covalent bonds between the reactive and co-reactive functional groups by a step growth process.

In another aspect this invention provides a reactive composition that crosslinks and produces no or minimal by-products on reaction, and that achieves crosslink density by step-growth addition process. This invention has several advantages. The composition is low in viscosity, readily melt processable and coatable, and has minimal residuals content such as solvents, monomers, plasticizers and/or viscosity modifiers. The compositions can be rapidly and reliably prepared without requiring specialized equipment and without generating concerns about potentially toxic or irritating unreacted low molecular weight monomeric species or reaction products.

In one embodiment, this invention provides medical articles and polymeric gel materials for use therein, which are preferably absorbent, and more preferably absorbent and transparent. By "gel" (or "polymer gel" or "polymeric gel material" or "hydrophilic gel") it is meant a gel material capable of swelling on contact with water (or aqueous fluids such as body fluids including blood, plasma, and intracellular fluid or fluids similar to body fluids such as physiological saline), but does not dissolve in water. The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is capable of absorbing fluids, particularly body fluids and preferably moderate to heavy amounts of body fluids, while retaining its structural integrity (i.e., remaining sufficiently intact such that it can perform the function of acting as a wound dressing).

Preferably the gel material is transparent and retains its transparency after absorption of fluids. By "transparent" it is meant that when the preferred material is applied to a patient (e.g., at a wound site), the area underlying the dressing can be visualized sufficiently to permit observation of the wound by a health care worker.

The term hydrophilic is used herein to describe oligomer compositions, which are capable of absorbing water exposed thereto in significant quantity, typically more than about 50% by weight, preferably 100% by weight, more preferably more than 200% by weight.

The application of water swelling polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, "medical" applications encompasses dental applications, including dental adhesives, restoratives, coatings, composites, sealants, etc. Because water swelling polymer gels have compositions and mechanical properties similar to those of biological tissues, such gels may be applied in a wide variety of fields in the future.

The ability to vary the crosslink density permits the modification of properties suitable for the various applications described previously. The novel compositions of the present invention cure by means of reactive and co-reactive polymerizable functional groups to form crosslinked compositions possessing tailorable properties such as strength, elasticity, absorbancy and toughness, for example, through selection of the particular constituents, and by control of the crosslink density. While the requirements for medical gels and flexible coatings, for example, are very different, the structure of the material and density of linkages can be altered while still maintaining the same method of forming crosslinked compositions. The maximum crosslink density is predetermined by the percentage of polymerizable functional groups incorporated into the crosslinkable composition. It may also be desirable to partially convert or cure a system for improved processing, while using a subsequent curing stage to obtain final properties.

As used herein, the term "melt processable" or simply "processable" is used to refer to oligomer compositions that possess or achieve a suitable low viscosity for coating or extrusion at temperatures less than or equal to 100° C., using conventional extrusion or coating equipment without the need for addition of solvents, monomers, plasticizers and/or viscosity modifiers and without the need for extraordinary pressures. The present invention provides compositions having less than two weight percent residuals.

As used herein, the term "step-growth process" means reaction to form a covalent bond between organic functional groups possessing a complementary reactivity relationship, i.e., electrophile-nucleophile. The process may occur by functional group rearrangement in the case of step-growth addition or by the elimination of a small molecule such as water or an alcohol in the case of step-growth condensation.

As used herein, the term "crosslinking" means the formation of a polymeric network of infinite molecular weight and occurs in polymerizations with monomer reactants having functionalities greater than two. Additional information may be found in G. Odian, *Principles of Polymerization,* 3rd edition, 1991, John Wiley & Sons: New York, p. 108. A crosslink is formed between the reactive and co-reactive functional groups by a step growth process.

Advantageously, the present invention provides crosslinkable compositions that are readily processed without appreciable residual content such as solvents, monomers, plasticizers and/or viscosity modifiers. Curable systems containing residual content can give rise to a significant increase in density when transformed from the uncured to the cured state causing a net shrinkage in volume. As is well known, shrinkage can cause a general loss of adhesion in many instances as well as significant movement and unpredictable registration. Shrinkage can also create residual stress in coatings, which can subsequently lead to mechanical failure.

The composition of the present invention minimizes shrinkage due to solvent evaporation and/or monomer polymerization. The low shrinkage compositions of this invention are particularly useful in dental, molding applications or in any applications where accurate molding and/or registration is required. The present invention provides a new class of reactive oligomers that may be formulated as 100% solids, cured by thermal means and that exhibit properties that meet or exceed those of solvent-borne or syrup polymers. The present invention provides compositions that exhibit less than 2% shrinkage, and preferably less than 1%.

Further, the purity of the materials and clean environment for processing are also important to produce high performance materials. Polymers used for coatings, gels and adhesives are often desirably delivered without significant amounts of volatile materials (such as monomeric species) to eliminate any contamination. However, the problems of residual volatile materials constitute a much more formidable challenge especially when acceptable limits of migratable, volatile impurities are on the order of a few parts per million. Industries such as medical and food packaging require materials of high purity and lower cost. The composition of the present invention avoids problems due to species contamination, having a residuals content of less than two weight percent, preferably less than one weight percent.

DETAILED DESCRIPTION OF THE INVENTION

The present invention provides crosslinkable compositions useful in the preparation of hydrophilic gels. The compositions are prepared from oligomers having pendent reactive functional groups and are formed from ethylenically unsaturated monomers. The compositions comprise a step growth curable oligomer composition comprising:

a) a first component oligomer, having a carbon-carbon backbone, comprising
a plurality of polymerized monomer units comprising pendant reactive
nucleophilic or electrophilic functional groups and pendent, hydrophilic poly(alkylene oxide) groups;
b) a second component oligomer co-reactive with said first component
oligomer, having a carbon-carbon backbone, comprising
a plurality of polymerized monomer units comprising pendent functional groups co-reactive with said pendant reactive nucleophilic or electrophilic functional groups of said first component oligomer and optionally, pendent, hydrophilic poly(alkylene oxide) groups;

wherein preferably at least one of a) and b) has a functionality of greater than 2 and wherein the composition is melt-processable at temperatures of 100° C. or less; and c) optionally a step growth catalyst.

The composition comprises, per 100 parts by weight of a first component, a sufficient amount of said second component to provide greater than two crosslinks per first component oligomer chain when cured or crosslinked. The relative amounts of said first and second component oligomers may vary widely; i.e. from 0.1 to 99.9 parts by weight of the first component oligomer and from 0.1 to 99.9 parts by weight of the second component oligomer. However, the relative amounts are chosen so that the crosslinked composition is hydrophilic, i.e. absorbs at least 50 wt. % water.

In one embodiment the first oligomer comprises:
(a) from 20 to 99.9 parts by weight of polymerized monomer units derived from ethylenically-unsaturated monomers having a pendent poly(alkylene oxide) group;
(b) from 0.1 to 35 parts by weight of polymerized monomer units derived from of an ethylenically-unsaturated monomer having a pendent reactive nucleophilic or electrophilic functional group;
(c) from 0 to 50 parts by weight of polymerized monomer units derived from polar monomer;
(d) from 0 to 20 parts by weight of polymerized monomer units derived from hydrophobic monomers;
(e) from 0 to 10 parts by weight of at least one other monomer.

In one embodiment the second component oligomer (b) comprises:
(a) from 0.1 to 35 parts by weight of polymerized monomer units derived from ethylenically-unsaturated monomers having a pendent co-reactive nucleophilic or electrophilic functional group;
(b) from 0 to 50 parts by weight of polymerized monomer units derived from polar monomers;

(c) from 0 to 20 parts by weight of polymerized monomers derived from hydrophobic monomers; and
(d) from 0 to 10 parts by weight of polymerized monomer units of at least one other monomer.

Optionally, the second component oligomer may further comprise from 20 to 99 parts by weight of polymerized monomer units derived from of an ethylenically-unsaturated monomer having a poly(alkylene oxide) group. Alternatively, the oligomeric composition may further contain a catalyst, such as a monomeric or polymeric acid catalyst, including photoacid generator.

The second component oligomer may be prepared in situ provided that, prior to crosslinking, the residual content is less than two wt. %, or the second component oligomer may be separately prepared and added to the oligomer mixture. The crosslinked composition of the invention results from a step growth process by reaction of the reactive and co-reactive functional groups. The first component oligomer and the second component oligomer may be the same component provided that the oligomer contains both reactive and co-reactive pendant functional groups. Preferably, the first component oligomer and second component oligomer are not the same component.

The first component oligomer, and optionally the second component oligomer, comprise polymerized monomer units derived from of an ethylenically-unsaturated monomer having pendent poly(alkylene oxide) group of the formula:

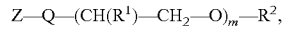

wherein Z is a polymerizable ethylenically unsaturated moiety, $R^1$ is a H or a $C_1$ to $C_4$ alkyl group, $R^2$ is a H, a $C_1$ to $C_4$ alkyl group, aryl group, or combinations thereof and m is from 2 to 100, preferably 5 to 20, and Q is a divalent linking group selected from —O—, —$NR^1$—, —$CO_2$— and —$CONR^1$. In one embodiment, the poly(alkylene oxide) group is a poly(ethylene oxide) (co)polymer. In another embodiment, the pendent poly(alkylene oxide) group is a poly(ethylene oxide-co-propylene oxide) copolymer. Such copolymers may be block copolymers, random copolymers, or gradient copolymers.

Useful ethylenically unsaturated moieties, Z, of the monomer may include:

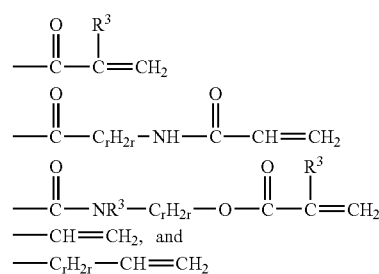

wherein $R^3$ is H or Me and r=1-10.

The monomer having a poly(alkylene oxide) group can be prepared, for example, by reacting mono- or di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxy groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

Useful functional monomers include unsaturated aliphatic, cycloaliphatic, and aromatic compounds having up to about 36 carbon atoms that include a functional group capable of further reaction, such as a hydroxyl, amino, alkyl halides, sulfonic esters, azlactone, oxazolinyl, 3-oxobutanoyl (i.e., acetoacetyl), carboxyl, isocyanato, epoxy, aziridinyl, acyl halide, or cyclic anhydride group.

Preferred functional monomers have the general formula:

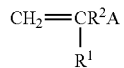

wherein $R^1$ is hydrogen, a $C_1$ to $C_4$ alkyl group, or a phenyl group, preferably hydrogen or a methyl group; $R^2$ is a single bond or a divalent linking group that joins an ethylenically unsaturated group to functional group A and preferably contains up to 34, preferably up to 18, more preferably up to 10, carbon and, optionally, oxygen and nitrogen atoms and, when $R^2$ is not a single bond, is preferably selected from

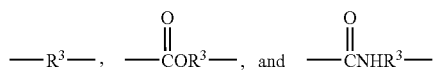

in which $R^3$ is an alkylene group having 1 to 6 carbon atoms, a 5- or 6-membered cycloalkylene group having 5 to 10 carbon atoms, or an alkylene-oxyalkylene in which each alkylene includes 1 to 6 carbon atoms or is a divalent aromatic group having 6 to 16 carbon atoms; and A is a functional group, capable of reaction with a co-reactive functional group (which is part of an unsaturated monomer) to form a covalent bond, preferably selected from the class consisting of hydroxyl, amino (especially secondary amino), carboxyl, isocyanato, aziridinyl, halides, sulfonic esters, epoxy, acyl halide, azlactone, oxazolinyl, acetoacetyl, and cyclic anhydride groups.

Representative hydroxyl group-substituted functional monomers include the hydroxyalkyl (meth)acrylates and hydroxyalkyl (meth)acrylamides such as 2-hydroxyethyl (meth)acrylate, 2-hydroxypropyl (meth)acrylate, 3-chloro-2-hydroxypropylmethyl (meth)acrylate, 2-hydroxyethyl (meth)acrylamide, 4-hydroxycyclohexyl (meth)acrylate, 3-acryloyloxyphenol, 2-(4-acryloyloxyphenyl)-2-(4-hydroxyphenyl)propane (also called bisphenol A monoacrylate), 2-propyn-1-ol, and 3-butyn-1-ol.

Representative amino group-substituted functional monomers include 2-methyl aminoethyl methacrylate, 3-aminopropyl methacrylate, 4-aminocyclohexyl methacrylate, N-(3-aminophenyl)acrylamide, 4-aminostyrene, N-acryloylethylenediamine, and 4-aminophenyl-4-acrylamidophenylsulfone.

Representative azlactone group-substituted functional monomers include 2-ethenyl- 1,3-oxazolin-5-one; 2-ethenyl-4-methyl- 1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5] spirodec-1-ene-4-one; 2-ethenyl-5,6-dihydro-4H-1,3-oxazin-6-one; 2-ethenyl-4,5,6,7-tetrahydro-1,3-oxazepin-7-one; 2-isopropenyl-5,6-dihydro-5,5-di(2-methylphenyl)-4H-1,3-oxazin-6-one; 2-acryloyloxy-1,3-oxazolin-5-one; 2-(2-acryloyloxy)ethyl-4,4-dimethyl-1,3-oxazolin-5-one; 2-ethenyl-4,5-dihydro-6H-1,3-oxazin-6-one, and 2-ethenyl-4,5-dihydro-4,4-dimethyl-6H-1,3-oxazin-6-one.

Representative oxazolinyl group-substituted functional monomers include 2-vinyl-2-oxazoline, 2-isopropenyl-2-oxazoline, 2-(5-hexenyl)-2-oxazoline, 2-acryloxy-2-oxazoline, 2-(4-acryloxyphenyl)-2-oxazoline, and 2-methacryloxy-2-oxazoline.

Representative acetoacetyl group-substituted functional monomers include 2-(acetoacetoxy)ethyl (meth)acrylate, styryl acetoacetate, isopropenyl acetoacetate, and hex-5-enyl acetoacetate.

Representative carboxyl group-substituted functional monomers include (meth)acrylic acid, 3-(meth)acryloyloxy-propionic acid, 4-(meth)acryloyloxy-butyric acid, 2-(meth) acryloyloxy-benzoic acid, 3-(meth)acryloyloxy-5-methyl benzoic acid, 4-(meth)acryloyloxymethyl-benzoic acid, phthalic acid mono-[2-(meth)acryloyloxy-ethyl]ester, 2-butenoic acid, and 4-pentenoic acid.

Representative isocyanate group-substituted functional monomers include 2-isocyanatoethyl(meth)acrylate, 3-isocyanatopropyl(meth)acrylate, 4-isocyanatocyclohexyl (meth)acrylate, 4-isocyanatostyrene, 2-methyl-2-propenoyl isocyanate, 4-(2-acryloyloxyethoxycarbonylamino)phenylisocyanate, allyl 2-isocyanatoethylether, and 3-isocyanato-1-propene.

Representative epoxy group-substituted functional monomers include glycidyl (meth)acrylate, thioglycidyl (meth) acrylate, 3-(2,3-epoxypropxy)phenyl (meth)acrylate, 2-[4-(2,3-epoxypropoxy)phenyl]-2-(4-acryloyloxy-phenyl) propane, 4-(2,3-epoxypropoxy)cyclohexyl(meth)acrylate, 2,3-epoxycyclohexyl (meth)acrylate, and 3,4-epoxycyclohexyl(meth)acrylate.

Representative aziridinyl group-substituted functional monomers include N-(meth)acryloylaziridine, 2-(1-aziridinyl)ethyl (meth)acrylate, 4-(1-aziridinyl)butyl(meth)acrylate, 2-[2-(1-aziridinyl)ethoxy]ethyl(meth)acrylate, 2-[2-(1-aziridinyl)ethoxycarbonylamino]ethyl(meth)acrylate, 1 2-[2-(2,2,3,3-tetramethyl-1-aziridinyl)ethoxycarbonylamino]dodecyl(meth)acrylate, and 1-(2-propenyl)aziridine.

Representative acyl halide group-substituted functional monomers include (meth)acryloyl chloride, a-chloroacryloyl chloride, acryloyloxyacetyl chloride, 5-hexenoyl chloride, 2-(acryloyloxy) propionyl chloride, 3-(acryloylthioxy) propionoyl chloride, and 3-(N-acryloyl-N-methylamino) propionoyl chloride.

Representative anhydride group-substituted functional monomers include maleic anhydride, acrylic anhydride, itaconic anhydride, 3-acryloyloxyphthalic anhydride, and 2-methacryloxycyclohexanedicarboxylic acid anhydride.

It will be understood in the context of the above description of the first and second component oligomers, that the ethylenically-unsaturated monomer possessing a reactive functional group ("reactive monomer") is chosen such that the first and second components are mutually co-reactive so that the first component oligomer has a pendant functional group that is co-reactive with the pendant functional group of the second component oligomer. The reactive and co-reactive functional groups form a crosslink between the first and second component oligomers by forming a linking group between the electrophilic and nucleophilic functional group pairs, and may include reactions commonly referred to as displacement, condensation and addition reactions, rather than polymerization of ethylenically-unsaturated groups.

While it is within the scope of the invention to employ nucleophile-electrophile combinations that react by displacement of some leaving group and creation of a by-product molecule, the removal of by-products may require an additional processing step. It is preferred that the nucleophile-electrophile combinations react by an addition reaction in which no by-product molecules are created, and the exemplified reaction partners react by this preferred mode. Exemplary combinations include hydroxyl or amino functional groups reacting with azlactone-, isocyanate-, and anhydride-functional groups and carboxyl groups reacting with isocyanate- and oxazoline-functional groups.

To aid in the understanding of this interaction between reactive first and co-reactive second functional groups, Table 1 summarizes some possible combinations of functional groups, using carboxyl and hydroxyl groups as representative examples. Those skilled in the art will readily recognize how other previously described functional groups also can be used to form covalent linking groups.

TABLE I

| Functional group | | Co-reactive functional group | | Resultant linking group |
|---|---|---|---|---|
| carboxyl | —COOH | oxazolinyl | (oxazoline ring with $R^{12}$ substituents) | $-CO-C(R^{12})(R^{12})-C(R^{12})(R^{12})-NHC(O)-$ |
| | | aziridinyl | (aziridine ring with $R^{12}$ substituents) | $-COC(R^{12})(R^{12})-C(R^{12})(R^{12})NH-$ |
| | | epoxy | (epoxide with $R^{12}$ substituents) | $-COC(R^{12})-C(OH)(R^{12})-$ |
| hydroxyl | —OH | isocyanato | O=C=N— | $-OC(O)NH-$ |
| | | acid halide | XC(O)— | $-OC(O)-$ |
| | | azlactone | (azlactone ring, n = 1 or 2) | $-OC(O)-(C(R^{12}))_n-NHC(O)-$ |
| | | (thio)epoxy | (thio)epoxide with G = O or S | $-OC(R^{12})-C(GH)(R^{12})-$ |

In Table I, each $R^{12}$ is independently hydrogen, an alkyl group having 1 to 4 carbon atoms, or a phenyl group.

The first component oligomer, and optionally the second component oligomer may comprise one or more polar monomers. As used herein "polar monomers" are those polymerizable monomers having a water miscibility (water in monomer) of at least 1 wt. %, preferably at least five weight % without reaching a cloud point and are exclusive of the poly(alkylene oxide) monomer.

Polar monomers can be used to increase the absorbency and/or improve the mechanical properties (e.g. the tensile strength) of the crosslinked polymer used in forming the gel material. Preferred polar monomers can also provide compliance to the resultant polymer. Examples of suitable polar monomers include N-vinyl caprolactam, N-vinyl acetamide, N-vinyl pyrrolidone, acrylonitrile, tetrahydrofurfuryl acrylate, acrylamide, mono- or di-N-alkyl substituted acrylamides, (meth)acrylic acid, itaconic acid, beta-carboxyethyl acrylate, glycerol methacrylate, [2-(meth)(acryloyloxy)ethyl]trimethylammonium chloride, [2-(meth)(acryloyloxy)ethyl]trimethylammonium methyl sulfate, and combinations thereof. Preferred polar monomers include N-vinyl pyrrolidone, N-vinyl acetamide, and mixtures thereof, and the like.

The first and second oligomers may further comprise hydrophobic monomers. Hydrophobic monomers can be used to reduce (and thereby better control) the absorbency of the polymer used in forming the gel material, and preferably improve the strength of the polymer.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_5$ - $C_{30}$ alkyl groups. Due to $T_g$ and sidechain crystallinity considerations, preferred are those having from $C_5$-$C_{12}$ alkyl groups, although use of $C_1$-$C_4$ and $C_{13}$-$C_{14}$ alkyl groups are also useful if the combinations provide a molecule averaged number of carbon atoms between $C_5$ and $C_{12}$. However, for many applications, $C_{12}$-$C_{30}$ alkyl groups may be preferred. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and diacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

The first and second component oligomers may further comprise other monomers. The selection of the "other monomers" useful in preparing the functional oligomer(s) (of the first and second components) is such that the ultimate crosslinked material has properties suitable for its application. For example, "other monomers" may be used to increase the tensile strength or other mechanical properties, or to control the $T_g$ of the polymer. Useful "other monomers" include vinyl monomers such as vinyl acetate, styrenes, and alkyl vinyl ethers, maleic anhydride and polyfunctional monomers. Use of minor amounts (e.g. one weight percent or less) of such other monomers is useful in controlling the modulus of the resulting polymer, and reducing the viscosity by creating a highly branched polymer.

Preferred first component oligomers used in forming the gel materials of the present invention include 20 to 99 parts by weight of the monomer units having a poly(alkylene oxide) group. More preferably, the first component oligomer comprises 50 to 99 parts by weight and most preferably 60 to 99 parts by weight of the monomer units having a poly(alkylene oxide) group.

Preferred second component oligomers may comprise 20 to 99 parts by weight of the monomer units having a poly(alkylene oxide) group. More preferably, the second component oligomer comprises 50 to 99 parts by weight and most preferably 60 to 99 parts by weight of the monomer units having a poly(alkylene oxide) group.

Preferred first and second component oligomers of the present invention include 0.1 to 35 parts by weight of the monomer units having a pendent (co)reactive functional group. More preferably, the first and second component oligomers comprise 0.5 to 35 parts by weight, and most preferably 0.5 to 5 parts by weight of the monomer units having a pendent (co)reactive functional group.

Preferred first and second component oligomers of the present invention may comprise 0 to 50 parts by weight of a polar monomer. More preferably, the polar monomer is used in an amount of no greater than about 35 parts by weight, based on the total weight of the oligomer. Most preferably, the polar monomer is used in an amount of no greater than about 30 parts by weight. Preferably, the polar monomer is used in an amount of at least about 5 parts by weight. More preferably, the polar monomer is used in an amount of at least about 10 parts by weight.

Preferred first and second component oligomers of the present invention include no greater than about 20 parts by weight of a hydrophobic monomer. Even more preferably, the hydrophobic monomer is used in an amount of no greater than about 10 parts by weight. Most preferably, the hydrophobic monomer is used in an amount of no greater than about 5 parts by weight of a hydrophobic monomer.

Preferred first and second component oligomers of the present invention include no greater than about 10 parts by weight of "other monomers", based on the total weight of the oligomer. More preferably, the functional monomer is used in an amount of less than 5 parts by weight, based on the total weight of the oligomer.

It will be understood in the context of the above description of the first and second oligomers, that the amount of monomer units having pendent poly(alkylene oxide) groups in the first and second component oligomers, and the relative amounts of the first and second component oligomers is such that the cured composition is hydrophilic, as previously defined.

Oligomers of the first and second components have relatively low molecular weight, then build molecular weight (and strength) by a step-growth process of the oligomers, through the pendent crosslinkable, reactive functional groups. As result of the relatively low molecular weight, the oligomers are easily processable in operations such as coating, spraying, extrusion and injection molding, because of the low melt viscosity prior to crosslinking, and without the need for solvents, plasticizers or viscosity modifiers. With the present oligomers, the slope of the log-log plot of viscosity vs. molecular weight ($M_n$) is about 1, whereas for high molecular weight polymers the slope is 3.4. The oligomers of the present invention provide processability, then crosslinking of the oligomers provides the needed physical properties such as toughness, hardness, impact resistance and others that are manifested in the cured state. Unless otherwise indicated molecular weight will refer to number average molecular weight.

A composition comprising oligomers of the first and second components have an average degree of polymerization (DP) generally less than about 300. The greater than expected viscosity (for polymers having a degree of polymerization greater than 300), is attributed to entanglements of polymer chains. It has been shown empirically that polymers or oligomers with less than 300 repeat units are not entangled. Prior to the present invention, unentangled polymers have been shown to be processable but-they have low strength. Preferably, both the first and second component oligomers have a degree of polymerization less than about 300.

If desired, higher molecular weight polymers may be blended with lower molecular weight oligomers so that the mixture has a viscosity of 500 to 10,000 cPs at temperatures less than 100° C.

Molecular weight may be controlled through the use of chain transfer agents, including mercaptans, disulfides, carbon alpha-methyl styrene, carbon tetrachloride, and others such as are known in the art. Useful chain transfer agents also include cobalt chelates, as described in U.S. Pat. Nos. 4,680,352 and 4,694,054, and oligomeric chain transfer agents as exemplified by

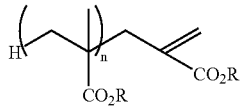

wherein each R is a lower alkyl group or a functional group (as previously described) and n is a number typically less than 10, as described in U.S. Pat. Nos. 5,362,826 and 5,773,534.

As previously described, the composition of the present invention comprises a first oligomer component with a plurality of pendent functional groups, a second component with a plurality of pendent co-reactive functional groups, and optionally a step-growth catalyst. The physical form of the composition may be a viscous liquid, a low melting solid or a powder, which is related to the glass transition temperature and the molecular weight. The amount of each monomer component and the relative amounts of the first and second component oligomers may be adjusted to obtain compositions having desired hydrophilicity, melt-processibility and mechanical properties. Due to the amount of poly(alkylene oxide) in the oligomers the oligomers are generally low melting solids or liquids.

The oligomers used in forming the gel material of the present invention can be produced by polymerizing the above-described monomers by conventional polymerization methods. Typical polymerization methods that can be used include thermal and/or photochemical as well as bulk and solution polymerization.

In a typical solution polymerization method, a monomer mixture is heated with stirring in the presence of a solvent and a polymerization initiator. Examples of the solvent are methanol, ethanol, isopropanol, acetone, methyl ethyl ketone, methyl acetate, ethyl acetate, toluene, xylene, and ethylene glycol alkyl ether. Those solvents can be used alone or as mixtures thereof. Examples of the polymerization initiator are benzoyl peroxide, cumene hydroperoxide, diisopropyl peroxydicarbonate, and 2,2'-azobisisobutyronitrile. Those polymerization initiators can be used alone or as mixtures thereof.

In a typical photopolymerization method, a monomer mixture is irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl- 1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 184 and 2959.

These photo- and thermal initiators can be employed in concentrations ranging from about 0.0001 to about 3.0 part by weight (pbw), preferably from about 0.001 to about 1.0 pbw, and more preferably from-about 0.005 to about 0.5 pbw, per 100 pbw of the monomer composition.

The first oligomer may be prepared (e.g., by solution polymerization followed by isolation) and then combined with a separately prepared second component. Any residual monomer and/or solvents used in the preparation are generally removed by conventional techniques such as distillation, vacuum evaporation, etc. Depending on the type of coating process to be used, the relative amounts of the oligomer(s) can vary greatly. The polymerizations may be conducted in the presence of suitable solvents such as ethyl acetate, toluene or tetrahydrofuran that are unreactive with the functional groups of the components of the first and second components.

Polymerization can be accomplished by exposing the component monomers to energy in the presence of a photoinitiator. Energy activated initiators may be unnecessary where, for example, ionizing radiation is used to initiate polymerization. These photoinitiators can be employed in concentrations ranging from about 0.0001 to about 3.0 pbw, preferably from about 0.001 to about 1.0 pbw, and more preferably from-about 0.005 to about 0.5 pbw, per 100 pbw of the composition.

The coatable oligomer composition is prepared by combining the two components containing the first oligomer, the second oligomer and optionally a catalyst. Partial conversion of the two components may be necessary to achieve a gel-free thickened solution exhibiting a coatable viscosity of from about 500-10,000 cPs at 22° C., more preferably from about 750 to 7500 cPs.

In general, the order of addition is conducted so as to minimize the reaction between the reactive and co-reactive functional groups prior to coating and thus maximize the useful shelf life or "open time", i.e. the time during which the composition is processed and applied to a substrate. Long open times are generally preferred. Shelf life refers to the amount of time the oligomer composition may be stored without premature gelation.

To avoid premature gelation it is generally advantageous to avoid having both reactive and co-reactive groups on the first oligomer component, or having both reactive and co-reactive groups on the second component. If the reactive and co-reactive groups are not highly reactive, i.e. do not react at appreciable rates at either ambient temperature or in the absence of a step-growth initiator, then one may accommodate the reactive and co-reactive groups on the first oligomer component. Similarly, if the relative concentrations of either the reactive or co-reactive function groups are low, then the two will not react at appreciable rates and gelation may be avoided. However, where the two do react at significant rates, gelation may be avoided by adding one of the components just prior to coating.

As is apparent to one skilled in the art, a portion-wise or sequential additional of the monomers may be desired in order to effectively incorporate monomers with different reactivity ratios, or to minimize the premature gelation, in order to prevent premature reaction between hydroxy and azlactone functional groups. The oligomer(s) may be prepared by sequential addition in which a mixture of a monomer containing a reactive functional group and other nonfunctional group containing monomers, is partially polymerized, then a monomer containing a co-reactive functional group is added, then further polymerizing the mixture.

Alternatively, one or more of the reactive functional groups may be converted to a "protected functional group" to render it temporarily unreactive or blocked. The protective groups may then be removed, either by thermal means, photochemical means, or by means of a selective reagent that reacts with the protective groups, but is otherwise unreactive with other moieties of functional groups in the composition. For example, hydroxyl groups may be converted to triimethylsilyl groups, processed as desired, then the protective trimethylsilyl group released by treatment with a fluoride reagent to allow crosslinking. The selection and use of protective groups is described in *Protective Groups in Organic Synthesis*, T. Greene and P. G. M. Wuts, Eds., 3rd edition, Wiley Interscience, N.Y, N.Y, 1999. Thus, at least one of the reactive and co-reactive functional groups may be protected functional groups.

The oligomer composition may be coated onto a substrate at useful and relatively time-stable thicknesses ranging from 25-500 micrometers or more. Stable thicknesses are necessary to maintain the desired coating thickness prior to reaction of the oligomer composition to form the crosslinked composition. Coating can be accomplished by any conventional means such as roller, dip, knife, or extrusion coating.

A preferred method of preparing a crosslinked article comprises partial conversion of the reactive and co-reactive functional groups to form linkages between the first and second components, coating the partially converted oligomer composition onto a substrate (such as a tape backing) and then further conversion of the reactive and co-reactive functional groups to obtain a fully crosslinked material. Partial conversion provides a coatable mixture of the first and second components.

The crosslinked composition is characterized as a polymer having a first oligomer chain having the residue of two or more pendent, functional groups chemically linked to the residue of two or more co-reactive functional groups that are pendent from a second component. At least one of the two components must have greater than two functional groups on average to achieve crosslinking. Thus, during exposure to thermal energy, the functional group reacts with a second, co-reactive functional group pendent from a second oligomer chain to form a crosslink (linkage) between the chains. The preferable molecular weight between crosslinks ($M_c$) will vary depending on application, where materials having higher ($M_c$) are generally softer. For example, for pressure-sensitive adhesives, the present crosslinked composition has effective molecular weight between crosslinks, ($M_c$), of greater than or equal to 1,000 and preferably greater than 3,000. Effective molecular weight between crosslinks ($M_c$), may be measured by dynamic mechanical analysis.

The number and concentration of pendent functional groups that are pendent from oligomer chains may easily control the degree of crosslinking. In general, the smaller the $M_c$, the lower the elasticity and hence the harder the film. On the other hand, films having a lower degree of crosslinking exhibit greater flexibility. Use of a stoichiometric excess of a component containing a functional group or a co-reactive functional group may be useful to control the extent of reaction between the reactive and co-reactive functional groups, under the above specified conditions, and thereby control the $M_c$. Stoichiometric excesses of even 10-fold represent minor amounts on a comparative weight basis relative to the whole composition.

Step-growth catalysts may be used to enhance rates of reaction between reactive and co-reactive functional groups and to effect the crosslinking of the components. Metal catalysts such as dibutyltin dilaurate and dibutyltin diacetate are effective with alcohol-isocyanate combinations. Strong acids such as ethanesulfonic acid, trifluoroacetic acid and methanesulfonic acid are useful with azlactone-alcohols and with the anhydride-alcohols. Effective concentrations of the catalytic agents are from 0.01 to 5.00 weight percent based on the concentration of the stoichiometrically limiting reactant. Strong bases include 1,8-diazabicyclo[5.4.0]undec-7-ene,(DBU), 1,5-diazabicyclo[4.3.0]non-5-ene (DBN), and N-methyl-1,5,7-triazabicyclo[4.4.0]dec-5-ene (MeTBD).

In addition to the ingredients mentioned above, the oligomer composition may include certain other materials such as pigments, plasticizers, tackifiers and reinforcing agents. However, the addition of any such material adds complexity and hence expense to an otherwise simple, straightforward, economical composition and process and is not preferred except to achieve specific results.

When the composition of the invention is used to prepare gel materials, the gel material of the present invention can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material of the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 84% per ASTM D1003-00). Typically, the amount of hydrocolloid, if used, is less than about five wt. %, based on the total weight of the gel material.

Other additives that can be incorporated into the gel material of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate), and alpha-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the gel material of the present invention is substantially free of plasticizers, including water. This is advantageous at least because special packaging is not required. Furthermore, plasticizers can migrate to other parts of a dressing, for example, which can be detrimental to the integrity of the dressing, or into the body of the patient on which the dressing is disposed.

Optionally, the gel material may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges that are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different than the pattern on the facing surface of the gel material, as can the size of the pattern elements. Further, the individual elements on either surface of the gel material may be protuberances extending from the surface or depressions in the surface.

If desired, the gel material may be in direct contact with the wound and/or skin surface. However, direct contact may be provided by other suitable hydrocolloid and hydrogel absorbent materials.

In a preferred medical article, the gel material forms a layer that is generally about 250 micrometers (i.e., microns) to about 5000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the oligomeric composition. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly and rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 400 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e. fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations means for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyether-amide, polyurethanes, chlorinated polyethylene, styrene/butadiene block copolymers (KRATON brand thermoplastic rubber, Shell Chemical Company, Houston, Tex.) and poly(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B.F. Goodrich, Cleveland, Ohio, elastomeric polyester such as those available under the trade designation HYTREL from E.I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 $g/m^2/24$ hrs, preferably about 3000 to 4000 $g/m^2/24$ hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in International Publication No. WO 00/42958.

Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. No. 4,499,896 (Heinecke); U.S. Pat. No. 4,598,004 (Heinecke); and 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive which can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration --A--B--A--- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), U.S. Pat. No. 6,518,343 (Lucast et al.) and U.S. Pat. No. 6,441,092 (Gieselman); multilayered adhesives as disclosed in U.S. Pat. No. 6,461,467 (Blatchford et al.). A particularly preferred adhesive includes 15 wt-% acrylic acid, 15 wt-% methoxypolyethylene oxide 400 acrylate, 70 wt-% isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the gel layer, i.e. the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYSLIK S-8004, 83 pound (135.4 g/m$^2$) bleached silicone release paper supplied by H. P. Smith Co., Chicago, Ill., and 80 pound (130.5 g/m$^2$) bleached two-sided silicone coated paper (2-80-BKG-157) supplied by Daubert Chemical Co., Dixon, Ill.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. No. 5,531,855 (Heinecke et al.) and U.S. Pat. No. 5,738,642 (Heinecke et al.).

An optional patterned surface may be imparted to the gel material by conventional molding techniques. Alternatively, a desired pattern may be imparted using an embossing technique. Examples of such techniques are described in International Publication No. WO 01/60296 A1.

EXAMPLES

Unless otherwise noted, all reagents and solvents were or can be obtained from Aldrich Chemical Co., Milwaukee, Wis.

As used herein,

"AMS" refers to alpha-methylstyrene;

"HEMA" refers to 2-hydroxyethyl methacrylate, available from Mitsubishi Rayon Co., Ltd., Tokyo, Japan;

"MPEG" refers to polyethylene glycol methyl ether methacrylate, $M_W$ approximately 400 g/mol, available from Osaka Organic Chemical Industry, Ltd., Osaka, Japan;

"VDM" refers to vinyl dimethyl azlactone, available from Groupe SNPE, Paris, France;

"DMACM" refers to N,N'-dimethyl acrylamide;

"DBU" refers to 1,8-diazabicyclo[5.4.0]undec-7-ene;

VAZO 52 refers to 2,2-azobis(2,4-dimethylpentanenitrile), available from E.I. du Pont de Nemours and Co., Wilmington, Del.;

Test Methods

Absorbency

The absorbency of each exemplary composition was determined by immersing a weighed 3 cm diameter disk of the composition, each having a thickness of approximately 1.1 mm, in approximately 200 mL of 0.9 weight percent aqueous NaCl. The weight of each sample was recorded as "dry weight." After 24 hours, each sample was removed from the solution and the excess liquid was allowed to drip off of the sample for 1 minute. The sample was again weighed and this weight was recorded as "wet weight." The absorbency of each sample was calculated as the increase in sample weight, expressed as a percentage of the dry weight, according to the formula:

100(wet weight−dry weight)/dry weight.

Preparative Example 1

Preparation of a Reactive Hydrophilic Copolymer of MPEG, HEMA, and AMS

A mixture of MPEG (99.9 g), HEMA (0.1 g) AMS (1.0 g), ethyl acetate (100 g) and VAZO 52 (0.4g) was placed in a screw cap glass jar. Nitrogen gas was bubbled through the mixture for approximately 20 minutes and then the jar was sealed with a cap. The jar was placed in a water bath shaker, in which the water temperature was maintained at 60° C., for 16 hours. The mixture was then allowed to cool to room temperature to afford a solution of the reactive hydrophilic copolymer.

Preparative Example 2

Preparation of a Reactive Hydrophilic Copolymer of MPEG, VDM, and AMS

A mixture of MPEG (99.9 g), VDM (0.1 g), AMS (1.0 g), ethyl acetate (100 g) and VAZO 52 (0.4 g) was placed in a screw cap glass jar. Nitrogen gas was bubbled through the mixture for approximately 20 minutes and then the jar was sealed with a cap. The jar was placed in a water bath shaker, in which the water temperature was maintained at 60° C., for 16 hours. The mixture was then allowed to cool to room temperature to afford a solution of the reactive hydrophilic copolymer.

Preparative Example 3

Preparation of a Reactive Hydrophilic Copolymer of MPEG, HEMA, and AMS

A mixture of MPEG (90 g), HEMA (10 g), AMS (1.0 g), ethyl acetate (10 g) and VAZO 52 (0.4 g) was placed in a screw cap glass jar. Nitrogen gas was bubbled through the mixture for approximately 20 minutes and then the jar was sealed with a cap. The jar was placed in a water bath shaker, in which the water temperature was maintained at 60° C., for 16 hours. The mixture was then allowed to cool to room temperature to afford a solution of the reactive hydrophilic copolymer.

Preparative Example 4

Preparation of a Reactive Hydrophilic Copolymer of MPEG, VDM, and AMS

A mixture of MPEG (90 g), VDM (10 g), AMS (1.0 g), ethyl acetate (10 g) and VAZO 52 (0.4 g) was placed in a screw cap glass jar. Nitrogen gas was bubbled through the mixture for approximately 20 minutes and then the jar was sealed with a cap. The jar was placed in a water bath shaker, in which the water temperature was maintained at 60° C., for 16 hours. The mixture was then allowed to cool to room temperature to afford a solution of the reactive hydrophilic copolymer.

Examples 1-8

Preparation of Crosslinked Compositions Comprising Reactive Hydrophilic Copolymers For each of Examples 1-8, two of the solutions of reactive hydrophilic copolymers of Preparative Examples 1-4, as indicated in Table 1, were combined in a glass vial. Each mixture was stirred gently with a wooden applicator stick until it appeared to be homogeneous. Each mixture was then allowed to stand at room temperature for approximately 30 minutes to allow any entrained air bubbles to escape, i.e., until each mixture was substantially free of entrained bubbles. DBU (5 mole percent, based on the total concentration of reactive groups in the mixture) was then added to each vial and each mixture was gently stirred. Each mixture was then coated onto a sheet of poly(ethylene terephthalate) (PET) release liner, such as those available under the trade designation "CLEARSIL", available from CPFilms, Martinsville, Va., and the solvent was evaporated by allowing the coating to stand at room temperature for approximately 24 hours. Each dry coating was then heated in an oven at 70° C. for 4 hours to crosslink the coating. Each crosslinked coating was then evaluated for absorbency as described. The data are given in Table 1. In Table 1, "N/A" means that the corresponding reactive hydrophilic oligomer was not included in the composition.

TABLE 1

Crosslinked Compositions of Examples 1–8*

| Example | Wt. of Oligomer from Preparative Example 1 | Wt. of Oligomer from Preparative Example 2 | Wt. of Oligomer from Preparative Example 3 | Weight of Oligomer from Preparative Example 4 | Absorbency |
|---|---|---|---|---|---|
| 1 | 3 g | N/A | N/A | 7 g | 1216% |
| 2 | N/A | 5 g | 5 g | N/A | 1356% |
| 3 | N/A | 7 g | 3 g | N/A | 1560% |
| 4 | N/A | N/A | 5 g | 5 g | 354% |
| 5 | N/A | N/A | 7 g | 3 g | 260% |
| 6 | N/A | N/A | 0.5 g | 9.5 g | 1054% |
| 7 | N/A | N/A | 3 g | 7 g | 1287% |
| 8 | N/A | N/A | 9.5 g | 0.5 g | 598% |

*weights are solids weight, typically coated as 50% solids

The invention claimed is:

1. A hydrophilic, step-growth curable oligomer composition comprising
   a) a first component oligomer comprising a plurality of polymerized ethylenically unsaturated monomer units comprising pendant reactive nucleophilic or electrophilic functional groups, and pendent, hydrophilic polyalkylene oxide groups;
   b) a second polyfunctional component co-reactive with said first component oligomer comprising a second oligomer comprising a plurality of polymerized ethylenically-unsaturated monomer units comprising pendant functional groups co-reactive with said pendant reactive nucleophilic or electrophilic functional groups of said first component oligomer.

2. The oligomer composition of claim 1 wherein the composition is melt-processable at temperatures of 100° C. or less.

3. The oligomer composition of claim 1 wherein at least one of a) and b) has a functionality of greater than 2.

4. The composition of claim 1 wherein said composition has a residual content of less than 2 weight %.

5. The composition of claim 1, wherein said pendent polyalkylene oxide groups of said first component oligomer is of the formula: —(CH(R$^1$)—CH$_2$—O)$_m$—R$^2$ wherein R$^1$ is a H or a C$_1$ to C$_4$ alkyl group, R$^2$ is H, a C$_1$ to C$_4$ alkyl group, aryl, or combinations thereof, and m is from 2 to 100.

6. The composition of claim 1, wherein said pendent poly(alkylene oxide) group is a poly(ethylene oxide) (co)polymer.

7. The composition of claim 1, wherein said pendent poly(alkylene oxide) group is a poly(ethylene oxide-co-propylene oxide) copolymer.

8. The composition of claim 1 which comprises an amount of said second component sufficient to provide more than two crosslinks per first component oligomer chain.

9. The composition of claim 1 which comprises
   (a) from 0.1 to 99.9 parts by weight of said first component oliogomer, and
   (b) from 99.9 to 0.1 parts by weight of said second component oligomer, wherein the composition, when crosslinked, can absorb at least 50 wt. % water.

10. The composition of claim 1 which comprises:
   (a) from 20 to 99.9 parts by weight of said first component oligomer, and
   (b) from 99.9 to 0.1 parts by weight of said second component oligomer.

11. The composition of claim 1 having a viscosity of 500 to 10,000 cPs at temperatures less than 100° C.

12. The composition of claim 1 wherein said first component oligomer comprises
   (a) from 20 to 99.9 parts by weight of polymerized ethylenically-unsaturated monomer units having a poly(alkylene oxide) group;
   (b) from 0.1 to 35 parts by weight of polymerized ethylenically-unsaturated monomer units having a pendent reactive nucleophilic or electrophilic functional group;
   (c) from 0 to 50 parts by weight of polymerized ethylenically-unsaturated polar monomer units, exclusive of the ethylenically-unsaturated monomer having a poly(alkylene oxide) group;
   (d) from 0 to 20 parts by weight of polymerized ethylenically-unsaturated hydrophobic monomer units;
   (e) from 0 to 10 parts by weight polymerized ethylenically-unsaturated monomer units of at least one other monomer.

13. The oligomer composition of claim 12 wherein said polar monomer, when present, is selected from the group consisting of substituted (meth)acrylamides, N-vinyl pyrrolidone, N-vinyl caprolactam, acrylonitrile, tetrahydrofurfuryl acrylate, acrylamides, and mixtures thereof.

14. The composition of claim 1 wherein said second component oligomer comprises
   (a) from 20 to 99 parts by weight of polymerized ethylenically-unsaturated monomer units having a pendent poly(alkylene oxide) group;
   (b) from 0.1 to 35 parts by weight of polymerized ethylenically-unsaturated monomer units having a pendent co-reactive nucleophilic or electrophilic functional group;
   (c) from 0 to 35 parts by weight of polymerized ethylenically-unsaturated polar monomer units, exclusive of the ethylenically-unsaturated monomer having a poly(alkylene oxide) group;
   (d) from 0 to 20 parts by weight of polymerized ethylenically-unsaturated hydrophobic monomer units;
   (e) from 0 to 10 parts by weight of polymerized ethylenically-unsaturated monomer units of at least one other monomer.

15. The composition of claim 1 further comprising a step-growth catalyst.

16. The composition of claim 1 wherein at least one of said reactive and co-reactive functional groups are protected functional groups.

17. The composition of claim 1, wherein said nucleophilic functional group of said ethylenically-unsaturated monomer having a nucleophilic functional group is selected from hydroxy, amino, isocyanato and azlactone functional groups.

18. A process for making a substrate bearing a coating of a crosslinked polymer composition on at least one surface thereof, comprising the steps of:
   (a) coating onto said substrate the oligomer composition of claim 1; and
   (b) thermally crosslinking said first oligomer component and second component by forming covalent bonds between said reactive groups of said first oligomer and co-reactive groups of said second component.

19. The process of claim 18 wherein said oligomer composition further comprises a step-growth catalyst.

20. The process of claim 18 wherein said oligomer composition has been partially converted to a coatable viscosity of from 750 to 7,500 cPs at 22° C. prior to step a.

21. The process of claim 18 wherein said oligomer composition comprises
   (a) per 100 parts by weight of said first component oligomer, an amount of said second component oligomer sufficient to provide more than two crosslinks per first component oligomer chain;
   (b) less than 2 parts by weight residuals content; and
   (c) from 0.0001 to about 3.0 parts by weight of a step-growth catalyst.

22. The process of claim 18 wherein said first component oligomer comprises:
   (a) from 20 to 99.9 parts by weight of polymerized ethylenically-unsaturated monomer units having a poly (alkylene oxide) group;
   (b) from 0.1 to 35 parts by weight of polymerized ethylenically-unsaturated monomer units having a pendent reactive nucleophilic or electrophilic functional group;
   (c) from 0 to 50 parts by weight of polymerized ethylenically-unsaturated polar monomer units, exclusive of the ethylenically-unsaturated monomer units having a poly(alkylene oxide) group;
   (d) from 0 to 20 parts by weight of polymerized ethylenically-unsaturated hydrophobic monomer units;
   (e) from 0 to 10 parts by weight of polymerized ethylenically-unsaturated monomer units of at least one other monomer.

23. The process of claim 22 wherein said polar monomer, when present, is selected from the group consisting of substituted (meth)acrylamides, N-vinyl pyrrolidone, N-vinyl caprolactam, acrylonitrile, tetrahydrofurfuryl acrylate, acrylamides, and mixtures thereof.

24. The process of claim 18 wherein said second component oligomer comprises
   (a) from 20 to 99 parts by weight of polymerized ethylenically-unsaturated monomer units having a pendent poly(alkylene oxide) group;
   (b) from 0.1 to 35 parts by weight of polymerized ethylenically-unsaturated monomer units having a pendent co-reactive nucleophilic or electrophilic functional group;
   (c) from 0 to 35 parts by weight of polymerized ethylenically-unsaturated polar monomer units, exclusive of the ethylenically-unsaturated monomer having a poly (alkylene oxide) group;
   (d) from 0 to 20 parts by weight of polymerized ethylenically-unsaturated hydrophobic monomer units derived from a hydrophobic monomer;
   (e) from 0 to 10 parts by weight ethylenically-unsaturated monomer units of at least one other monomer.

25. The process of claim 24 wherein said hydrophobic monomers, when present, comprise acrylic esters of non-tertiary alkyl alcohols having 5 to 12 carbon atoms.

26. The process of claim 18 wherein at least one of said reactive and co-reactive functional groups are protected functional groups.

27. The process of claim 18 wherein the molecular weight ($M_n$) of said first oligomer is less than the entanglement molecular weight.

28. The process of claim 27 wherein the molecular weight of said first component oligomer is controlled with a chain transfer agent.

29. The process of claim 28 wherein said chain transfer agent is alpha methylstyrene.

30. The process of claim 18 wherein said pendant reactive functional group is a hydroxyl functional group and said pendant co-reactive functional group is selected from the group of an anhydride functional groups and an azlactone functional groups.

31. The process of claim 22 wherein said pendant reactive functional group is an azlactone group.

32. The process of claim 22 wherein said pendant reactive functional group is a hydroxyl group.

33. A process for making a substrate bearing a coating of a crosslinked polymer composition on at least one surface thereof, comprising the steps of:
   (1) coating onto said curable oligomer composition of claim 1; and
   (2) crosslinking said first oligomer component and second component by forming covalent bonds between said reactive groups of said first component oligomer and co-reactive groups of said second component.

34. The process of claim 33 wherein said step (2) of crosslinking is in the presence of a catalyst.

35. The process of claim 34 wherein said catalyst is a step-growth catalyst.

36. The process of claim 3 wherein said catalyst is an acid catalyst.

37. An absorbent dressing comprising a crosslinked hydrophilic gel absorbent layer of claim 1.

38. The absorbent dressing of claim 37 comprising:
   a permeable facing layer,
   a backing layer bonded to said facing layer at the periphery, and
   a hydrophilic gel absorbent layer disposed between the backing and facing layer.

39. The absorbent dressing of claim 37 having a layer of pressure sensitive adhesive on at least a portion of the front surface of the facing layer.

40. The absorbent dressing of claim 37 wherein the gel layer further comprises a pharmacologically active agent.

41. The absorbent dressing of claim 37 wherein the gel layer further comprises a hydrocolloid.

42. The absorbent dressing of claim 37 wherein the gel layer further comprises a patterned surface.

* * * * *

UNITED STATES PATENT AND TRADEMARK OFFICE
CERTIFICATE OF CORRECTION

PATENT NO. : 7,384,984 B2
APPLICATION NO. : 10/732715
DATED : June 10, 2008
INVENTOR(S) : Kevin M. Lewandowski It is certified that error appears in the above-identified patent and that said Letters Patent is hereby corrected as shown below:

Title Page
Item [56], under "Other Publications", Line 5, delete "Oduin," and insert -- Odian, --, therefor.

Item [56], under "Other Publications", Line 8, delete "GIbov," and insert -- Gibov, --, therefor.

Item [56], under "Other Publications", Line 9, delete "Jerusaled," and insert -- Jerusalem, --, therefor.

Item [56], under "Other Publications", Line 16, delete "Havign" and insert -- Having --, therefor.

Column 13
Line 7, delete "but-they" and insert -- but they --, therefor.

Column 15
Line 23, delete "triimethylsilyl" and insert -- trimethylsilyl --, therefor.

Column 16
Line 1, delete "M,," and insert -- $M_c$, --, therefor.

Column 22
Line 54, delete "H. P." and insert -- H.P. --, therefor.

Column 23
Line 17, delete "$M_w$approximately" and insert -- $M_w$ approximately --, therefor.

Line 48, delete "(0.1 g)" and insert -- (0.1 g), --, therefor.

UNITED STATES PATENT AND TRADEMARK OFFICE
CERTIFICATE OF CORRECTION

PATENT NO. : 7,384,984 B2
APPLICATION NO. : 10/732715
DATED : June 10, 2008
INVENTOR(S) : Kevin M. Lewandowski It is certified that error appears in the above-identified patent and that said Letters Patent is hereby corrected as shown below:

<u>Column 24</u>
Line 13, delete "(10 g)" and insert -- (l00g) --, therefor.

Line 28, delete "(10 g)" and insert -- (l00g) --, therefor.

<u>Column 25</u>
Line 40, in claim 4, after "residual" insert -- monomer and solvent --.

Line 57, in claim 9, delete "oliogomer," and insert -- oligomer, --, therefor.

<u>Column 27</u>
Line 23, in claim 21, after "residual" insert -- monomer and solvent --.

Line 37, in claim 22, after "monomer" delete "units".

Signed and Sealed this

Twenty-sixth Day of May, 2009

JOHN DOLL
*Acting Director of the United States Patent and Trademark Office*